US009023339B2

(12) United States Patent
Reed et al.

(10) Patent No.: US 9,023,339 B2
(45) Date of Patent: May 5, 2015

(54) BIOCONTROL OF NEMATODES

(71) Applicant: Bayer CropScience LP, Research Triangle Park, NC (US)

(72) Inventors: Nathan Royalty Reed, Davis, CA (US); Philip Thomas Varghese, Davis, CA (US)

(73) Assignee: Bayer CropScience LP, Research Triangle Park, NC (US)

( * ) Notice: Subject to any disclaimer, the term of this patent is extended or adjusted under 35 U.S.C. 154(b) by 0 days.

(21) Appl. No.: 13/667,186

(22) Filed: Nov. 2, 2012

(65) Prior Publication Data

US 2013/0142759 A1 Jun. 6, 2013

Related U.S. Application Data

(60) Provisional application No. 61/556,001, filed on Nov. 4, 2011.

(51) Int. Cl.
*A01N 63/02* (2006.01)
*A01N 63/00* (2006.01)

(52) U.S. Cl.
CPC .............. *A01N 63/02* (2013.01); *A01N 63/00* (2013.01)

(58) Field of Classification Search
CPC ............................. A01N 63/00; A01N 63/02
USPC ............................ 424/93.2, 93.46; 435/252.5
See application file for complete search history.

(56) References Cited

U.S. PATENT DOCUMENTS

| | | | |
|---|---|---|---|
| 6,015,553 A | 1/2000 | Germida et al. | |
| 6,060,051 A | 5/2000 | Heins et al. | |
| 6,103,228 A | 8/2000 | Heins et al. | |
| 6,291,426 B1 | 9/2001 | Heins et al. | |
| 6,417,163 B1 | 7/2002 | Heins et al. | |
| 6,524,998 B1 | 2/2003 | Kloepper et al. | |
| 6,638,910 B2 | 10/2003 | Heins et al. | |
| 6,896,883 B2 | 5/2005 | Bergstrom et al. | |
| 2010/0048647 A1* | 2/2010 | Suwa ........................... | 514/357 |

FOREIGN PATENT DOCUMENTS

| | | | |
|---|---|---|---|
| EP | 2460407 A1 | 6/2012 | |
| WO | 9910477 A1 | 3/1999 | |
| WO | WO 99/10477 A1 | 3/1999 | |
| WO | WO9910477 | * | 3/1999 |
| WO | 0029426 A1 | 5/2000 | |
| WO | WO 00/29426 A1 | 5/2000 | |
| WO | 0058442 A1 | 10/2000 | |
| WO | WO 00/58442 A1 | 10/2000 | |
| WO | WO2010030554 | * | 3/2010 |
| WO | WO2010030554 A1 | 3/2010 | |
| WO | WO2010128003 A2 | 11/2010 | |
| WO | WO2012087980 A1 | 6/2012 | |

OTHER PUBLICATIONS

The International Search Report and the Written Opinion of the International Searching Authority for International Application No. PCT/US2012/063195, mailed Feb. 12, 2013, entire document.
Dawar, S., et al., "Application of Bacillus Species in Control of Meloidogyne javanica (Treub) Chitwood on Cowpea and Mash Bean", Pak. J. Bot., 2008, 40:439-444.
Kokalis-Burelle, N., et al., "Field Evaluation of Plant Growth-Promoting Rhizobacteria Amended Transplant Mixes and Soil Solarization for Tomato and Pepper Production in Florida", Plant and Soil, 2002, 238:257-266.
Lian, L.H., et al., "Proteases from Bacillus: a New Insight into the Mechanism of Action for Rhizobacterial Suppression of Nematode Populations", Letters of Applied Microbiology, 2007, 45:262-269.
Lobna, M. & Zawam, H., "Efficacy of some Biocontrol Agents on Reproduction and Development of Meloidogyne incognita Infecting Tomato", Journal of American Science, 2010, 6:495-509.
Siddiqui, Z.A. & Akhtar, M.S., "Effects of Antagonistic Fungi, Plant Growth-Promoting Rhizobacteria, and Arbuscular Mycorrhizal Fungi Alone and in Combination on the Reproduction of Meloidogyne incognita and Growth of Tomato", J. Gen. Plant Pathol., 2009, 75:144-153.
Tariq, M. & Dawar, S., "Impact of Biocontrol Bacteria with Rhizophora mucronata Plant Parts in Suppression of Meloidogyne javanica (treub) Chitwood on Crop Plants", Archives of Phytopathology and Plant Protection, 2010, 43:754-760.
Tian, B., et al., "Bacteria Used in the Biological Control of Plant-Parasitic Nematodes: Populations, Mechanisms of Action, and Future Prospects", FEMS Microbiol. Ecol., 2007, 61:197-213.
Choudhary, D. K., et al., "Interactions of Bacillus spp. and plants—With special reference to induced systemic resistance (ISR)," Microbiological Research, vol. 64, No. 5, pp. 493-513, Sep. 29, 2009.
Merckling, T., et al., "AgraQuest: Development of Serenade as a biopesticide against plant bacterial diseases," Annual COST873 Meeting—Management Committee Meeting, 35 pp., Oct. 26, 2009.
Niknam, G. R., et al., "Induction of Systemic Resistance by Bacillus Subtilis Isolate Bst Against Rotylenchulus Reniformis in Tomato," Nematologia Mediterranea, vol. 31, No. 2, pp. 239-243, Jan. 1, 2003.
International Search Report & Written Opinion of the International Searching Authority, PCT/US2012/047963, dated Nov. 23, 2012, 13 pages.
AgraQuest "Senerade® Max product sheet", available online Sep. 10, 2010.
International Search Report & Written Opinion of the International Searching Authority, PCT/US2012/063195, dated Feb. 12, 2013, 10 pages.

* cited by examiner

*Primary Examiner* — Janet Epps-Smith
*Assistant Examiner* — Courtney Brown
(74) *Attorney, Agent, or Firm* — Michelle L. Samonek; Adam L. Lunceford

(57) ABSTRACT

A method for controlling nematodes in or on a plant, a plant part, and/or a locus for plant growth is provided, the method comprising applying to a plant, plant part, or locus for plant growth in need of protection from said nematodes an effective amount of *Bacillus pumilus*, a mutant of *Bacillus pumilus*, or at least one metabolite of *Bacillus pumilus*. In particular, the *Bacillus pumilus* strain may be strain QST2808.

19 Claims, No Drawings

BIOCONTROL OF NEMATODES

BACKGROUND OF INVENTION

Plant parasitic nematodes cause significant damage to a wide variety of crops, resulting in global crop yield losses estimated to range from 5% to 12% annually. Root damage by nematodes is very common and leads to stunted plants that have smaller root systems, show symptoms of mineral deficiencies in their leaves, and wilt easily. Damage by nematodes also predisposes plants to infection by a wide variety of plant pathogenic fungi and bacteria.

In order to combat and control nematodes, farmers typically use chemical nematicides. These range from gas and liquid fumigation, such as methyl bromide and chloropicrin, to application of organophosphates and carbamates, such as thionazin and oxamyl. Use of these chemical nematicides has been ongoing for several decades. Despite the effectiveness of the chemical nematicide in controlling target nematodes, there are serious limitations to these methods. One limitation is that chemical nematicides cannot act against nematodes that have already penetrated the root. Another limitation is the danger associated with the production and use of chemical nematicides. Chemical nematicides are highly toxic and can lead to human poisoning and death. As a result, countries have restricted and sometimes banned certain pesticides. For example, methyl bromide is banned in most countries due to its ozone-depleting effects.

Because of these restrictions and bans, there is a lack of viable nematode solutions. The present disclosure provides a safe and effective means to replace or lessen the use of chemical pesticides. The disclosure is also unique in providing a solution that both inhibits penetration of nematodes into the plant root and prevents maturation of those nematodes that manage to overcome this initial barrier.

SUMMARY OF INVENTION

The present disclosure provides methods and compositions for the control of plant parasitic nematodes. The disclosure provides a method for controlling nematodes comprising applying to a plant, a plant part or a locus of the plant an effective amount of *Bacillus pumilus*, mutants of *Bacillus pumilus*, spores of *Bacillus pumilus*, or metabolites of *Bacillus pumilus*, and particularly *Bacillus pumilus* QST2808, mutants of *Bacillus pumilus* QST2808, spores of *Bacillus pumilus* QST2808, or metabolites of *Bacillus pumilus* QST2808. In some embodiments, the *Bacillus pumilus* (e.g., *Bacillus pumilus* QST2808) is applied as a fermentation product that includes the *Bacillus pumilus*, its metabolites and, optionally, residual fermentation broth.

In some embodiments, the target nematodes are disease causing root knot nematodes. In certain instances, the nematodes are from the species *Meloidogyne*. The present compositions kill eggs of root knot nematodes, decrease root knot nematode plant penetration, and/or inhibit maturation of root knot nematodes that penetrate plants.

In other embodiments, the target nematodes are cyst nematodes. In certain instances, the nematodes are from the species *Heterodera*. In other instances, the nematodes are from the species *Globodera*.

In some embodiments, the above-described compositions are mixed with at least one other pesticide, such as a fungicide, insecticide, nematicide or herbicide. In one embodiment, the pesticide is a nematicide. In certain embodiments the *Bacillus pumilus* QST2808-based nematicide is tank mixed with a commercially available formulated nematicide. In other embodiments, the *Bacillus pumilus*-based composition (e.g., *Bacillus pumilus* QST2808) is mixed with the at least one other pesticide and then formulated, such that the multiple actives form one product.

The present disclosure further provides any of the compositions of the present disclosure further comprising a formulation inert or other formulation ingredient, such as polysaccharides (starches, maltodextrins, methylcelluloses, proteins, such as whey protein, peptides, gums), sugars (lactose, trehalose, sucrose), lipids (lecithin, vegetable oils, mineral oils), salts (sodium chloride, calcium carbonate, sodium citrate), and silicates (clays, amorphous silica, fumed/precipitated silicas, silicate salts). In some embodiments, such as those in which the compositions are applied to soil, the compositions of the present disclosure comprise a carrier, such as water or a mineral or organic material such as peat that facilitates incorporation of the compositions into the soil. In some embodiments, such as those in which the composition is used for seed treatment or as a root dip, the carrier is a binder or sticker that facilitates adherence of the composition to the seed or root. In another embodiment in which the compositions are used as a seed treatment the formulation ingredient is a colorant. In other compositions, the formulation ingredient is a preservative.

In some embodiments the compositions are applied to plants, plant parts, or loci of the plants, such as soil, prior to planting. In other embodiments that compositions are applied at planting. In still others the compositions are applied after planting.

In certain embodiments, application of the compositions is preceded by a step comprising identifying that the plant or plant locus for growth needs treatment. In some embodiments, identifying includes determining that the locus for plant growth exceeds the economic threshold for nematode infestation.

In some embodiments, the present disclosure encompasses a kit that includes *Bacillus pumilus* and instructions for its use as a nematicide. Preferably, said *Bacillus pumilus* is *Bacillus pumilus* QST2808. In some embodiments these instructions are a product label. In some embodiments, these instructions are for use of the *Bacillus pumilus* QST2808 as a nematicide in combination with a chemical nematicide. In certain instances, the instructions direct the user to use the chemical nematicide at a rate that is lower than the rate recommended on a product label for the chemical nematicide when used as a stand-alone treatment.

DETAILED DESCRIPTION OF THE INVENTION

All publications, patents, and patent applications, including any drawings and appendices herein, are incorporated by reference to the same extent as if each individual publication or patent application was specifically and individually indicated to be incorporated by reference.

The following description includes information that may be useful in understanding the present disclosure. It is not an admission that any of the information provided herein is prior art or relevant to the presently claimed inventions, or that any publication specifically or implicitly referenced is prior art.

*Bacillus pumilus* QST2808, its mutants, supernatants, and methods for their use to control plant pathogens and insects are fully described in U.S. Pat. Nos. 6,245,551 and 6,586,231; each of which is specifically and entirely incorporated by reference herein for everything it teaches. In these U.S. patents, the strain is referred to as NRRL No. B-30087, which is synonymous with QST2808. *Bacillus pumilus* QST2808 was deposited with the NRRL on Jan. 14, 1999, under the provisions of the Budapest Treaty on the International Recognition of the Deposit of Microorganisms for the Purpose of Patent Procedure under Accession Number B-30087. Any references in this specification to QST2808 refer to *Bacillus pumilus* QST2808.

The term "mutant" refers to a genetic variant derived from *Bacillus pumilus*. In one embodiment, the mutant has one or more or all the identifying (functional) characteristics of *Bacillus pumilus*. In another embodiment, the mutant has one or more or all the identifying (functional) characteristics of *Bacillus pumilus* strain QST2808. In a particular instance, the mutant or a fermentation product thereof controls (as an identifying functional characteristic) nematodes at least as well as the parent *Bacillus pumilus* (e.g., the parent *Bacillus pumilus* QST2808 strain). Such mutants may be genetic variants having a genomic sequence that has greater than about 85%, greater than about 90%, greater than about 95%, greater than about 98%, or greater than about 99% sequence identity to *Bacillus pumilus*, and especially to *Bacillus pumilus* strain QST2808. Mutants may be obtained by treating *Bacillus pumilus* cells, and especially *Bacillus pumilus* strain QST2808 cells with chemicals or irradiation or by selecting spontaneous mutants from a population of such cells (such as phage resistant or antibiotic resistant mutants) or by other means well known to those practiced in the art. In some embodiments, the term mutant excludes *Bacillus pumilus* cells having a loss of function mutation in the swrA gene.

Compositions of the present disclosure can be obtained by culturing *Bacillus pumilus*, and particularly *Bacillus pumilus* strain QST2808, according to methods well known in the art, including use of the media and other methods described in U.S. Pat. No. 6,245,551. Conventional large-scale microbial culture processes include submerged fermentation, solid state fermentation, or liquid surface culture. Towards the end of fermentation, as nutrients are depleted, *Bacillus pumilus* cells begin the transition from growth phase to sporulation phase, such that the final product of fermentation is largely spores, metabolites, and residual fermentation medium. Sporulation is part of the natural life cycle of *Bacillus pumilus* and is generally initiated by the cell in response to nutrient limitation. Fermentation is configured to obtain high levels of colony forming units ("cfu") of *Bacillus pumilus* and to promote sporulation. The bacterial cells, spores, and metabolites in culture media resulting from fermentation may be used directly or concentrated by conventional industrial methods, such as centrifugation, tangential-flow filtration, depth filtration, and evaporation. Fermentation broth and broth concentrate are both referred to herein as "fermentation products." Compositions of the present disclosure include fermentation products. In some embodiments, the concentrated fermentation broth is washed, for example, via a diafiltration process, to remove residual fermentation broth and metabolites.

The fermentation broth or broth concentrate can be dried with or without the addition of carriers using conventional drying processes or methods including, but not limited to, spray drying, freeze drying, tray drying, fluidized-bed drying, drum drying, or evaporation.

The resulting dry products may be further processed, such as by milling or granulation, for example, to achieve a specific particle size (e.g., an average particle size of about 1 to about 5,000, about 1 to about 2,500, about 1 to about 500, about 1 to about 250, about 1 to about 100, about 1 to about 50, about 1 to about 25, about 1 to about 10 μm, or any other particle size or range thereof desired and known in the art) or physical format. Carriers, described below, may also be added post-drying.

Cell-free preparations of fermentation broth of the novel variants and strains of *Bacillus* of the present disclosure can be obtained by any means known in the art, such as extraction, centrifugation and/or filtration of fermentation broth. Those of skill in the art will appreciate that so-called cell-free preparations may not be devoid of cells, but rather are largely cell-free or essentially cell-free, depending on the technique used (e.g., speed of centrifugation) to remove the cells. The resulting cell-free preparation may be dried and/or formulated with components that aid in its application to plants or to plant growth media. Concentration methods and drying techniques described above for fermentation broth are also applicable to cell-free preparations.

Metabolites of *Bacillus pumilus*, including *Bacillus pumilus* strain QST2808, can be obtained according to the methods set forth in U.S. Pat. No. 6,245,551. The term "metabolites" as used herein may refer to semi-pure and pure or essentially pure metabolites, or to metabolites that have not been separated from *Bacillus pumilus*.

Concentration methods and drying techniques described above for formulation of fermentation broth are also applicable to metabolites.

Compositions of the present disclosure may include formulation inerts added to compositions comprising cells, cell-free preparations, or metabolites to improve, efficacy, stability, and usability and/or to facilitate processing, packaging, and end-use application. Such formulation inerts and ingredients may include carriers, stabilization agents, nutrients, or physical property modifying agents, which may be added individually or in combination. In some embodiments, the carriers may include liquid materials such as water, oil, and other organic or inorganic solvents and solid materials such as minerals, polymers, or polymer complexes derived biologically or by chemical synthesis. In some embodiments, the carrier is a binder or adhesive that facilitates adherence of the composition to a plant part, such as a seed or root. See, e.g., Taylor, A. G., et al., "Concepts and Technologies of Selected Seed Treatments", Annu Rev. Phytopathol. 28: 321-339 (1990), which is specifically and entirely incorporated by reference herein for everything it teaches. The stabilization agents may include anti-caking agents, anti-oxidation agents, desiccants, protectants, or preservatives. The nutrients may include carbon, nitrogen, and phosphors sources such as sugars, polysaccharides, oil, proteins, amino acids, fatty acids, and phosphates. The physical property modifiers may include bulking agents, wetting agents, thickeners, pH modifiers, rheology modifiers, dispersants, adjuvants, surfactants, antifreeze agents, or colorants. In some embodiments, the composition comprising cells, cell-free preparation, or metabolites produced by fermentation can be used directly with or without water as the diluent without any other formulation preparation. In some embodiments, the formulation inerts are added after concentrating fermentation broth and during and/or after drying.

Compositions of the present disclosure may include carriers, which are inert formulation ingredients added to fermentation products or cell-free preparations to improve recovery, efficacy, or physical properties and/or to aid in packaging and administration. Such carriers may be added individually or in combination.

The compositions of the present disclosure may be mixed with other chemical and non-chemical additives, adjuvants, and/or treatments, wherein such treatments include but are not limited to chemical and non-chemical fungicides, insecticides, miticides, nematicides, fertilizers, nutrients, minerals, auxins, growth stimulants, and the like.

Nematicides with which the *Bacillus pumilus*-based compositions of the present disclosure may be mixed may be chemical or biological nematicides. The term "chemical nematicide," as used herein, excludes fumigants, and the term "fumigants" encompasses broad spectrum pesticidal chemicals that are applied to soil pre-planting and that diffuse through the soil (in soil air and/or soil water) and may be applied as gases, such as methyl bromide, volatile liquids, such as chloropicrin, or volatile solids, such as dazomet.

In some embodiments, the chemical or biological nematicide is a commercially available formulated product and is tank mixed with the compositions of the present disclosure. In other embodiments, the chemical or biological nematicide is mixed with the *Bacillus pumilus*-based composition (e.g., from *Bacillus pumilus* QST2808) prior to formulation such that the compositions form one formulated product.

Chemical nematicides used in such mixtures are carbamates, oxime carbamates, and organophosphorous nematicides. Carbamate nematicides include benomyl, carbofuran (FURADAN®), carbosulfan and cloethocarb. Oxime carbamates include alanycarb, aldicarb (TEMIK® or as part of the AVICTA® Complete Pak seed treatment from Syngenta), aldoxycarb (STANDAK®), oxamyl (VYDATE®), thiodicarb (part of the AERIS® seed-applied system from Bayer CropScience), and tirpate. Organophosphorous nematicides include fensulfothion (DANSANIT®), ethoprop (MOCAP®), diamidafos, fenamiphos, fosthietan, phosphamidon, cadusafos, chlorpyrifos, dichlofenthion, dimethoate, fosthiazate, heterophos, isamidofos, isazofos, phorate, phosphocarb, terbufos, thionazin, triazophos, imicyafos, and mecarphon. Parenthetical names following each compound are representative commercial formulations of each of the above chemicals. Other chemical nematicides useful for such mixtures include spirotetramat)(MOVENTO®, MON37400® nematicide and fipronil.

Biological nematicides include chitin and urea mixtures; compost extracts and teas (both aerated and nonaerated); compositions comprising the fungus *Myrothecium* verrucaria and/or metabolites therefrom (commercially available as DITERA®); compositions comprising the fungus Paecilomyces, including *P. lilacinus* (commercially available as, for example, MELOCON® or BIOACT®); compositions comprising the bacterium Pasteuria, including *P. usgae* (commercially available as, for example, ECONEM®); compositions comprising bacteria from the *Bacillus* sp., including *Bacillus firmus* (such as strain CNMCI-1582, deposited with the Collection Nationale de Cultures de Microorganismes, Institute Pasteur, France on May 29, 1995 and commercially available as, for example, VOTIVO®), *Bacillus subtilis, Bacillus amyloliquefaciens*, and *Bacillus cereus*; and compositions comprising nematicidal *Streptomycete* sp., such as *Streptomyces lydicus* (commercially available as ACTINOVATE®). Biological nematicides also include botanically-based nematicides such as products based on neem plants (including seeds or oil from the plants) or azidirachtin, a secondary metabolite of neem seeds, sesame oil-based products (such as DRAGONFIRE®), carvacrol, and products based on plant extracts (such as NEMA-Q®, obtained from the *Quillaja saponaria* tree of Chile). Biological nematicides also include isolated compounds produced by bacteria, such as the mectins, which are produced by *Streptomyces* avermentilis, including abamectin (consisting of a combination of abamectin $B_{1a}$ and $B_{1b}$) and avermectin $B_{2a}$, and the harpin proteins, originally identified in *Erwinia amylovora*, including $harpin_{EA}$ and $harpin_{\alpha\beta}$.

Compositions of the present disclosure are useful to control plant parasitic nematodes, such as, for example, root-knot, cyst, lesion and ring nematodes, including *Meloidogyne* spp., *Heterodera* spp., *Globodera* spp., *Pratylenchus* spp. and *Criconemella* sp. Compositions are also useful to control *Tylenchulus semipenetrans, Trichodorus* spp., *Longidorus* spp., *Rotylenchulus* spp., *Xiphinema* spp., *Belonolaimus* spp. (such as *B. longicaudatus*), *Criconemoides* spp., *Tylenchorhynchus* spp., *Hoplolaimus* spp., *Rotylenchus* spp., *Helicotylenchus* spp., *Radopholus* spp. (such as *R. citrophilis* and *R. similis*), *Ditylenchus* spp., and other plant parasitic nematodes. In some embodiments the targets are cyst nematodes, such as *Heterodera glycines* (soybean cyst nematodes), *Heterodera schachtii* (beet cyst nematode), *Heterodera avenae* (Cereal cyst nematode), *Meloidigyne incognita* (Cotton (or southern) root knot nematode), *Globodera rostochiensis*, and *Globodera pallida* (potato cyst nematodes). In other embodiments, the targets are root knot nematodes, such as *M. incognita* (cotton root knot nematode), *M. javanica* (Javanese root knot nematode), *M. hapla* (Northern root knot nematode), and *M. arenaria* (peanut root knot nematode).

The term "control," as used herein, means killing, reducing in numbers, and/or reducing growth, feeding or normal physiological development of any or all life stages of nematodes (including, for root knot nematodes, the ability to penetrate roots and to develop within roots), reduction of the effects of nematode infection and/or infestation (e.g., galling, penetration, and/or development within roots), resistance of a plant to infection and/or infestation by nematodes, resistance of a plant to the effects of nematode infection and/or infestation (e.g., galling and/or penetration), tolerance of a plant to infection and/or infestation by nematodes, tolerance of a plant to the effects of nematode infection and/or infestation (e.g., galling and/or penetration), or any combination thereof. The resistance to and tolerance of plants to parasitic nematodes has been known to those of ordinary skill in the art, as demonstrated by Trudgill, D. L. "Resistance to and Tolerance of Plant Parasitic Nematodes in Plants." Annual Review of Phytopathology. 1991; 29:167-192, which is specifically and entirely incorporated by reference herein for everything it teaches. An effective amount is an amount able to noticeably reduce pest growth, feeding, root penetration, maturation in the root, and/or general normal physiological development and symptoms resulting from nematode infection. In some embodiments symptoms and/or nematodes are reduced by at least about 5%, at least about 10%, at least about 20%, at least about 30%, at least about 40%, at least about 50%, at least about 60%, at least about 70%, at least about 80%, or at least about 90% versus untreated controls.

Compositions of the present disclosure are used to treat a wide variety of agricultural and/or horticultural crops, including those grown for seed, produce, and landscaping. Representative plants that can be treated using the compositions of the present disclosure include but are not limited to the following: bulb vegetables; cereal grains; citrus fruits (such as grapefruit, lemon, and orange); cotton and other fiber crops; curcurbits; fruiting vegetables; leafy vegetables (such as celery, head and leaf lettuce, and spinach); legumes; oil seed crops; peanut; pome fruit (such as apple and pear); stone fruits (such as almond, pecan, and walnut); root vegetables; tuber vegetables; corm vegetables; tobacco, strawberry and other berries; cole crops (such as broccoli and cabbage); grape; pineapple; flowering plants; bedding plants; and ornamentals (such as fern and hosta). Compositions of the present disclosure are also used to treat perennial plants, including plantation crops, such as banana and coffee, and those present in forests, parks, or landscaping.

Compositions described herein are applied to a plant, a plant part, such as a seed, root, rhizome, corm, bulb, or tuber, and/or a locus on which the plant or the plant parts grow, such as soil, in order to control plant parasitic nematodes. The compositions of the present disclosure may be administered as a foliar spray, as a seed/root/tuber/rhizome/bulb/corm treatment, and/or as a soil treatment. The seeds/root/tubers/rhizomes/bulbs/corms, foliage, and/or soil can be treated before planting, during planting, or after planting.

Compositions described herein are also applied to a plant, a plant part, such as a seed, root rhizome, corm, bulb, or tuber, and/or a locus on which the plant or the plant parts grow, such as soil, in order to increase crop yield. In some embodiments, crop yield is increased by at least about 5%, in others by at least about 10%, in still others at least about 15%, and in still others by at least about 20%. In some embodiments, root weight is increased by at least about 5%, in others by at least about 10%, in still others at least about 15%, and in still others by at least about 20%.

When used as a seed treatment, the compositions of the present disclosure are applied at a rate of about $1 \times 10^2$ to about $1 \times 10^9$ cfu/seed, depending on the size of the seed. In some embodiments, the application rate is $1 \times 10^4$ to about $1 \times 10^7$ cfu/seed. In some embodiments, the application rate is about $1 \times 10^2$ to about $1 \times 10^8$, about $1 \times 10^2$ to about $1 \times 10^7$, about $1 \times 10^2$ to about $1 \times 10^6$, about $1 \times 10^2$ to about $1 \times 10^5$, about $1 \times 10^2$ to about $1 \times 10^4$, about $1 \times 10^2$ to about $1 \times 10^3$, about $1 \times 10^3$ to about $1 \times 10^5$, or preferably about $1 \times 10^4$ cfu/seed. When said compositions are combined or used with at least one additional active ingredient ("ai"), the at least one additional active may be present in an amount from about 0.001 to about 1000 grams, from about 0.01 to about 500 grams, from about 0.1 to about 300 grams, from about 1 to about 100 grams, from about 1 to about 50 grams, from about 1 to about 25 grams, and preferably from about 1 to about 10 grams per 100 kg of seed, and/or about $1 \times 10^2$ to about $1 \times 10^8$, about $1 \times 10^2$ to about $1 \times 10^7$, about $1 \times 10^2$ to about $1 \times 10^6$, about $1 \times 10^2$ to about $1 \times 10^5$, about $1 \times 10^2$ to about $1 \times 10^4$, about $1 \times 10^2$ to about $1 \times 10^3$, about $1 \times 10^3$ to about $1 \times 10^5$, or preferably about $1 \times 10^4$ cfu/seed.

The present compositions may also be applied as a root dip at a rate of about $1 \times 10^3$ to about $1 \times 10^8$ cfu/plant root system. When said compositions are combined or used with at least one additional active ingredient, the at least one additional active may be present in an amount from about 0.001 to about 1000 mg, about 0.01 to about 500, about 0.1 to about 400, about 1 to about 300, about 10 to about 250, and preferably from about 25 to about 200 mg ai/L, and/or about $1 \times 10^3$ to about $1 \times 10^8$ cfu/plant root system.

When used as a soil treatment, the compositions of the present disclosure can be applied as a soil surface drench, shanked-in, injected and/or applied in-furrow or by mixture with irrigation water. The rate of application for drench soil treatments, which may be applied at planting, during or after seeding, or after transplanting and at any stage of plant growth, is about $4 \times 10^7$ to about $8 \times 10^{14}$, about $4 \times 10^9$ to about $8 \times 10^{13}$, about $4 \times 10^{11}$ to about $8 \times 10^{12}$ about $2 \times 10^{12}$ to about $6 \times 10^{13}$, about $2 \times 10^{12}$ to about $3 \times 10^{13}$, or about $4 \times 10^{13}$ to about $2 \times 10^{14}$ cfu per acre. In some embodiments, the rate of application is about $1 \times 10^{12}$ to about $6 \times 10^{12}$ or about $1 \times 10^{13}$ to about $6 \times 10^{13}$ cfu per acre. The rate of application for in-furrow treatments, applied at planting, is about $2.5 \times 10^{10}$ to about $5 \times 10^{11}$ cfu per 1000 row feet. In some embodiments, the rate of application is about $6 \times 10^{10}$ to about $3 \times 10^{12}$, about $6 \times 10^{10}$ to about $4 \times 10^{11}$, about $6 \times 10^{11}$ to about $3 \times 10^{12}$, or about $6 \times 10^{11}$ to about $4 \times 10^{12}$ cfu per 1000 row feet. The rate of application when shanked or injected into soil is about $4 \times 10^7$ to about $8 \times 10^{14}$, about $4 \times 10^{13}$ to about $2 \times 10^{14}$ about $4 \times 10^8$ to about $8 \times 10^{13}$, about $4 \times 10^9$ to about $8 \times 10^{12}$ about $2 \times 10^{10}$ to about $6 \times 10^{11}$, about $4 \times 10^7$ to about $8 \times 10^{13}$, about $4 \times 10^7$ to about $8 \times 10^{12}$, about $4 \times 10^7$ to about $8 \times 10^{11}$, about $4 \times 10^7$ to about $8 \times 10^{10}$, about $4 \times 10^7$ to about $8 \times 10^9$, or about $4 \times 10^7$ to about $8 \times 10^8$ cfu per acre. Those of skill in the art will understand how to adjust rates for broadcast treatments (where applications are at a lower rate but made more often) and other less common soil treatments. When said compositions are combined or used with at least one additional active ingredient, the at least one additional active may be present in an amount from about 10 to about 1,000, about 10 to about 750, about 10 to about 500, about 25 to about 500, about 25 to about 250, and preferably from about 50 to about 200 g ai/ha, and/or about $4 \times 10^7$ to about $8 \times 10^{14}$, about $4 \times 10^{13}$ to about $2 \times 10^{14}$ about $4 \times 10^8$ to about $8 \times 10^{13}$, about $4 \times 10^9$ to about $8 \times 10^{12}$ about $2 \times 10^{10}$ to about $6 \times 10^{11}$, about $4 \times 10^7$ to about $8 \times 10^{13}$, about $4 \times 10^7$ to about $8 \times 10^{12}$, about $4 \times 10^7$ to about $8 \times 10^{11}$, about $4 \times 10^7$ to about $8 \times 10^{10}$, about $4 \times 10^7$ to about $8 \times 10^9$, or about $4 \times 10^7$ to about $8 \times 10^8$ cfu per acre.

The compositions of the present disclosure can be introduced to the soil before planting or before germination of the seed. The compositions of the present disclosure can also be introduced to the loci of the plants, to the soil in contact with plant roots, to soil at the base of the plant, or to the soil around the base of the plant (e.g., within a distance of about 5 cm, about 10 cm, about 15 cm, about 20 cm, about 25 cm, about 30 cm, about 35 cm, about 40 cm, about 45 cm, about 50 cm, about 55 cm, about 60 cm, about 65 cm, about 70 cm, about 75 cm, about 80 cm, about 85 cm, about 90 cm, about 95 cm, about 100 cm, or more around or below the base of the plant). The compositions may be applied by utilizing a variety of techniques including, but not limited to, drip irrigation, sprinklers, soil injection or soil drenching. The compositions may also be applied to soil and/or plants in plug trays or to seedlings prior to transplanting to a different plant locus. When applied to the soil in contact with the plant roots, to the base of the plant, or to the soil within a specific distance around the base of the plant, including as a soil drench treatment, the composition may be applied as a single application or as multiple applications. The compositions (including those with at least one additional active ingredient) may be applied at the rates set forth above for drench treatments or at a rate of about $1 \times 10^5$ to about $1 \times 10^8$ cfu per gram of soil, $1 \times 10^5$ to about $1 \times 10^7$ cfu per gram of soil, $1 \times 10^5$ to about $1 \times 10^6$ cfu per gram of soil, $7 \times 10^5$ to about $1 \times 10^7$ cfu per gram of soil, $1 \times 10^6$ to about $5 \times 10^6$ cfu per gram of soil, or $1 \times 10^5$ to about $3 \times 10^6$ cfu per gram of soil, and/or about $4 \times 10^7$ to about $8 \times 10^{14}$, about $4 \times 10^8$ to about $8 \times 10^{13}$, about $4 \times 10^9$ to about $8 \times 10^{12}$ about $2 \times 10^{10}$ to about $6 \times 10^{11}$, about $4 \times 10^7$ to about $8 \times 10^{13}$, about $4 \times 10^7$ to about $8 \times 10^{12}$, about $4 \times 10^7$ to about $8 \times 10^{11}$, about $4 \times 10^7$ to about $8 \times 10^{10}$, about $4 \times 10^7$ to about $8 \times 10^9$, or about $4 \times 10^7$ to about $8 \times 10^8$ cfu per acre. In one embodiment, the compositions of the present disclosure are applied as a single application at a rate of about $7 \times 10^5$ to about $1 \times 10^7$ cfu per gram of soil. In another embodiment, the compositions of the present disclosure are applied as a single application at a rate of about $1 \times 10^6$ to about $5 \times 10^6$ cfu per gram of soil. In other embodiments, the compositions of the present disclosure are applied as multiple applications at a rate of about $1 \times 10^5$ to about $3 \times 10^6$ cfu per gram of soil.

Preferably, the *Bacillus pumilus*-based composition of the present disclosure is about 1% w/w to about 99% w/w based on the entire formulation. More preferably, the *Bacillus pumilus*-based composition is present in an amount of about 1% w/w to about 80% w/w, about 1% w/w to about 60% w/w, about 1% w/w to about 50% w/w, about 1% w/w to about 40% w/w, about 1% w/w to about 30% w/w, about 1% w/w to about 20% w/w, about 1% w/w to about 10% w/w, and most preferably about 5% w/w to about 50% w/w.

*Bacillus pumilus*-based compositions of the present disclosure may be applied independently or in combination with one or more other nematicides, such as chemical and biological nematicides. In some embodiments, *Bacillus pumilus* QST2808 is co-formulated with at least one other nematicide and the co-formulated product is applied to the plant or plant locus. In some other embodiments, the *Bacillus pumilus*-based compositions are tank mixed with commercially available formulations of the chemical or biological nematicides and applied to plants and plant loci. In other embodiments, the *Bacillus pumilus*-based compositions of the present disclosure are applied to plants and/or plant loci immediately before or after the commercially available formulations of the chemical or biological nematicides. In other embodiments, the *Bacillus pumilus*-based compositions of the present disclosure are applied to plants and/or plant loci in rotation with the commercially available formulations of the chemical or biological nematicides. In one instance, the *Bacillus pumilus*-based compositions are applied as a seed treatment or as an in-furrow or drench treatment, as discussed in more detail below. In some instances of the above embodiments, the commercially available formulations of the chemical or biological nematicides are applied at a rate that is less than the rate recommended on the product label for use of such nematicides as stand-alone treatments, for example about 1%, about 2%, about 5%, about 10%, about 15%, about 20%, about 25%, about 35%, about 45%, about 50%, about 60%, about 70%, about 75%, about 80%, about 90%, or about 95% less.

In other embodiments, the *Bacillus*-based compositions of the present disclosure are applied to plants and/or plant loci following application of a fumigant. Fumigants can be applied by shank injection, generally a minimum of 8 inches below the soil surface. Liquid formulations of fumigants can also be applied through surface drip chemigation to move the fumigant to a depth of 8 inches or more below the soil surface. Treated soil beds are covered with a plastic tarp to retain the fumigant in the soil for several days. This is done before planting and then the soil is allowed to air out prior to planting. The *Bacillus*-based compositions described herein may be applied after such air-out period either prior to, at the time of, or post-planting. In some instances, the fumigants are applied at a rate that is less than the rate recommended on the product label.

Chemical and biological nematicides are described above. Example commercial formulations of each of the below fumigants are provided in parentheses after the chemical name(s). Fumigant nematicides include halogenated hydrocarbons, such as chloropicrin (CHLOR-O-PIC®); methyl bromide (METH-O-GAS®) and combinations thereof (such as BROM-O-GAS® and TERR-O-GAS®); 1,3-dichloropropene (TELONE® II, TELONE® EC, CURFEW®) and combinations of 1,3-dichloropropene with chloropicrin (TELONE® C-17, TELONE® C-35, and INLINE®) 1,2-dichloropropene; methyl iodide (MIDAS®) methyl isocyanate liberators, such as sodium methyl dithiocarbamate (VAPAM®, SOILPREP®, METAM-SODIUM®) and dazomet; combinations of 1,3 dichloropropoene and methyl isothiocyanate (VORLEX®); and carbon disulfide liberators, such as sodium tetrathiocarbonate (ENZONE®); and dimethyl disulphide or DMDS (PALADINO®).

Compositions of the present disclosure may also be applied as part of an integrated pest management ("IPM") program. Such programs are described in various publications, especially by university cooperative extensions. Such programs include crop rotation with crops that cannot host the target nematode, cultural and tillage practices, and use of transplants. For example, the *Bacillus*-based compositions could be applied after a season of growth with mustard or other nematode suppressive crop.

In some embodiments, application of the compositions of the present disclosure to plants, plant parts, or plant loci is preceded by identification of a locus in need of treatment. Such identification may occur through visual identification of plants that appear chlorotic, stunted, necrotic, or wilted (i.e., that appear to have nutrient deficiencies) typically coupled with knowledge of a history of nematode problems; plant sampling; and/or soil sampling. Plant sampling may occur during the growing season or immediately after final harvest. Plants are removed from soil and their roots examined to determine the nature and extent of the nematode problem within a field. For root knot nematode, root gall severity is determined by measuring the proportion of the root system which is galled. Galls caused by root knot nematodes may be distinguished from nodules of nitrogen-fixing soil bacteria because galls are not easily separated from the root. Root knot nematode soil population levels increase with root gall severity. In some instances, the detection of any level of root galling suggests a root knot nematode problem for planting any susceptible crop, especially in or near the area of sampling. Cyst nematodes may also be identified by plant sampling and scrutiny of roots for cysts.

Soil sampling offers a means to determine the number of nematodes and/or nematode eggs infesting a certain volume of soil or roots. Soil sampling may be conducted when a problem is first suspected, at final harvest, or any time prior to planting a new crop, including prior to crop destruction of the previous crop. University cooperative extension programs offer soil sampling services, including the University of Florida, Oregon State University, and the University of Nebraska-Lincoln. In addition, such programs provide guidance for how to collect samples. For example, in one method of post-harvest predictive sampling, samples are collected at a soil depth of 6 to 10 inches from 10 to 20 field locations over 5 or 10 acres (depending on value of the crop, with fewer acres sampled for higher value crops) in a regular zigzag pattern. In a method of testing established plants, root and soil samples are removed at a soil depth of 6 to 10 inches from suspect plants that are symptomatic but that are not dead or dying, i.e., decomposing.

In some embodiments, identification involves determining whether an economic threshold of nematode infestation has been reached, i.e., a point at which expected economic losses without treatment exceed treatment costs. The economic threshold varies depending on the crop, geography, climate, time of planting, soil type, and/or soil temperature. Numerous papers have been published on this topic and guidelines are available from university cooperative extension programs in different areas. See, e.g., Robb, J. G., et al., "Factors Affecting the Economic Threshold for *Heterodera schachtii* Control in Sugar Beet," Economics of Nematode Control, January-June 1992; Hafez, Saad L., "Management of Sugar Beet Nematode," University of Idaho Current Information Series (CIS), 1071 (1998); and "UC IPM Pest Management Guidelines: Tomato", UC ANR Publication 3470 Nematodes A. Ploeg, Nematology, UC Riverside (January 2008), each of which is specifically and entirely incorporated by reference herein for everything it teaches. Determining the economic threshold for a particular crop at a particular time of year is well within the skill set of one of ordinary skill in the art.

In some embodiments, the soil sampling reveals that the nematode infestation will cause yield that is about 80%, about 90%, or about 95% of normal for uninfested soil.

In some embodiments, the economic threshold of root knot juveniles per kilogram (kg) of soil sample is at least about 250, at least about 300, at least about 500, at least about 750, at least about 1000, at least about 2000, at least about 3000, at least about 4000, at least about 5000, or at least about 6000.

In some embodiments, the economic threshold of cyst nematode eggs and larvae per 1 cm$^3$ of soil is at least about 0.5, at least about 1, at least about 2, at least about 3, at least about 4. According to Hafez (1998), supra, a cyst may be estimated as 500 viable eggs and larvae.

The following examples are given for purely illustrative and non-limiting purposes of the present disclosure.

EXAMPLES

Example 1

Studies were conducted with cucumber seeds var. Sultan to determine activity of QST2808 against *Meloidogyne javanica*, root knot nematode. For this study, 50 ml centrifuge tubes containing 20 g sand and one ungerminated seed pre-treated with QST2808 whole broth were used.

250 ml flasks containing 75 ml of 8 g TSB based Schaeffer's media (TSB 8 g/L; 10% KCl(w/v), 10 ml/L; 1.2% MgSO$_4$ 7H$_2$O (w/v), 10 ml/L; 1M Ca(NO$_3$)$_2$, 1.0 ml/L; 0.010 M MnCl$_2$, 1.0 ml/L; 1 mM FeSO$_4$,1.0 ml/L) were inoculated with QST2808. Inoculated flasks were incubated for 2 days at 30° C., shaking at ~200 rpm. Optical density was measured and seeds coated with the desired number of colony forming units (see Table 2) and dried.

The treated seeds were allowed to germinate and grow in the greenhouse. Four to five days after treatment ("DAT") each tube was inoculated with 100 second-stage juvenile root knot nematodes. At 10 DAT, the seedlings were scored for percentage root galling on a 0-4 scale, which is described in Table 1.

The roots were then stained with acid fuschin to observe nematode penetration and development (see Table 2) and observed under a Leica dissecting microscope. For nematode penetration, the total nematode juveniles inside each root were counted. For nematode development, total fat juveniles including late second stage juvenile (J2's) and third stage juvenile (J3's) were counted. Penetration of nematodes into the root and nematode development after penetration were scored as detailed in Table 1. For details on techniques used, see C. O. Omwega, et al., "A Nondestructive Technique for Screening Bean Germ Plasm for Resistance to *Meloidogyne incognita*," Plant Disease (1988) 72(11): 970-972, which is specifically and entirely incorporated by reference herein for everything it teaches.

TABLE 1

Rating Scheme for Nematode Antagonistic Activity of Bacterial Whole Broths. The galling index was based on the percentage of root galling.

| Galling Index | |
|---|---|
| 0 | None |
| 1 | 1-24% |
| 2 | 25-49% |
| 3 | 50-74% |
| 4 | >75% |

TABLE 2

Results of seed pre-treatment with *Bacillus pumilus* QST2808

| CFU of QST2808 | Galling Index | Penetration | Development |
|---|---|---|---|
| 1 × 10$^3$ | 0.75 | 28.50 | 9.00 |
| 1 × 10$^4$ | 0.75 | 24.00 | 4.50 |
| 1 × 10$^5$ | 1.25 | 26.25 | 8.00 |
| 1 × 10$^6$ | 1.00 | 27.50 | 6.75 |
| 1 × 10$^7$ | 1.50 | 30.00 | 13.25 |
| Untreated Control | 2.75 | 36.25 | 23.50 |

The degree of development (total number of fat nematodes) between CFU rates 1×10$^3$ to 1×10$^6$ was not significantly different, but was significantly different from untreated controls and 1×10$^7$ CFU. The penetration data demonstrate a similar, though less robust trend. The galling index increase with increasing CFUs may be due to increasing root mass.

Example 2

Studies were conducted with cucumber seeds var. Sultan to determine activity of QST2808 against *Meloidogyne javanica*, root knot nematode. For this study, ungerminated seed pre-treated with QST2808 spores at the rate of 10$^4$ CFU were planted in sand in 32 oz. cups.

To obtain the spores, 250 ml flasks containing 75 ml of 8 g TSB based Schaeffer's media (TSB 8 g/L; 10% KCl(w/v), 10 ml/L; 1.2% MgSO$_4$ 7H$_2$O (w/v), 10 ml/L; 1M Ca(NO$_3$)$_2$,1.0 ml/L; 0.010M MnCl$_2$, 1.0 ml/L; 1 mM FeSO$_4$,1.0 ml/L) were inoculated with QST2808. Inoculated flasks were incubated for 2 days at 30° C., shaking at ~200 rpm. Optical density was measured and seeds coated with the desired number of colony forming units and dried.

The treated seeds were planted in 32 oz. pots and allowed to germinate and grow in the greenhouse. About 30 days after planting, the soil of each plant was inoculated with about 2000 second stage juvenile root knot nematodes. Roots were harvested about 4 weeks post inoculation and were weighed, assessed for disease severity and rated as to galling. Disease severity was rated on a scale of 0-3, where 0=no symptoms and 3=severe symptoms of root rotting and discoloration. Galling was rated using the method described in Bridge, J. and Page, S. J. L., Tropical Pest Management 26(3) 1980 pp. 296-298. Roots of QST2808-treated seeds look bigger and healthier than untreated control and roots treated by other bacterial candidates. Quantitative results—which suggest that *B. pumilus* may promote tolerance to nematodes—are shown in Table 3 below.

TABLE 3

|  | Disease severity (0-3 scale) | Fresh Root Wt. (g) | SD Fresh RWt | Gall rating (0-10 scale) Bridge & Page, 1989 | estimated total eggs/root |
|---|---|---|---|---|---|
| UTC | 3.0 | 4.793333 | 3.080817 | Non-scorable | 0.00 |
| Candidate 1 | 2.7 | 8.82 | 3.053981 | Non-scorable | 0.00 |
| Candidate 2 | 3.0 | 3.753333 | 1.581845 | 1 | 0.00 |
| Candidate 3 | 0.0 | 18.70667 | 5.861777 | 1.333333 | 233.33 |

We claim:

1. A method for controlling nematodes in or on a plant, plant part, and/or a locus for plant growth comprising applying to a plant, plant part, or locus for plant growth in need of protection from said nematodes an effective amount of *Bacillus pumilus* QST2808, a mutant of *Bacillus pumilus* QST2808, or at least one metabolite of *Bacillus pumilus* QST2808.

2. The method of claim 1 wherein the applying is preceded by the step of identifying that the plant, plant part, or locus for plant growth needs protection from said nematodes.

3. The method of claim 2 wherein the identifying comprises determining that the locus for plant growth exceeds an economic threshold for nematode infestation.

4. The method of claim 1 wherein the locus is soil.

5. The method of claim 4 wherein the *Bacillus pumilus* QST2808 is applied pre-planting.

6. The method of claim 4 wherein the *Bacillus pumilus* QST2808 is applied at planting.

7. The method of claim 4 wherein the *Bacillus pumilus* QST2808 is applied post-planting.

8. The method of claim 1 wherein the *Bacillus pumilus* QST2808 is applied at a rate of about $4 \times 10^7$ to about $8 \times 10^{14}$ cfu per acre.

9. The method of claim 1 wherein the *Bacillus pumilus* QST2808 is applied to seed.

10. The method of claim 1 wherein the *Bacillus pumilus* QST2808 is a fermentation product.

11. The method of claim 1 wherein the fermentation product comprises *Bacillus pumilus* QST2808, metabolites, and residual fermentation broth.

12. The method of claim 1 further comprising applying a second nematicide.

13. The method of claim 12 wherein the second nematicide is a chemical nematicide selected from the group consisting of a carbamate, an organophosphate, and combinations thereof.

14. The method of claim 12 wherein the second nematicide is applied in combination with the *Bacillus pumilus* QST2808.

15. The method of claim 12 wherein the second nematicide is applied in rotation with the *Bacillus pumilus* QST2808.

16. The method of claim 14 wherein the second nematicide is a formulated commercially available product.

17. The method of claim 16 wherein the second nematicide is applied at a rate that is less than the rate recommended on a product label for the second nematicide were the second nematicide applied as a stand-alone treatment.

18. The method of claim 1 wherein the nematodes are root-knot disease causing nematodes.

19. The method of claim 18 wherein the nematodes are from the species *Meloidogyne*.

* * * * *